Figure 1:
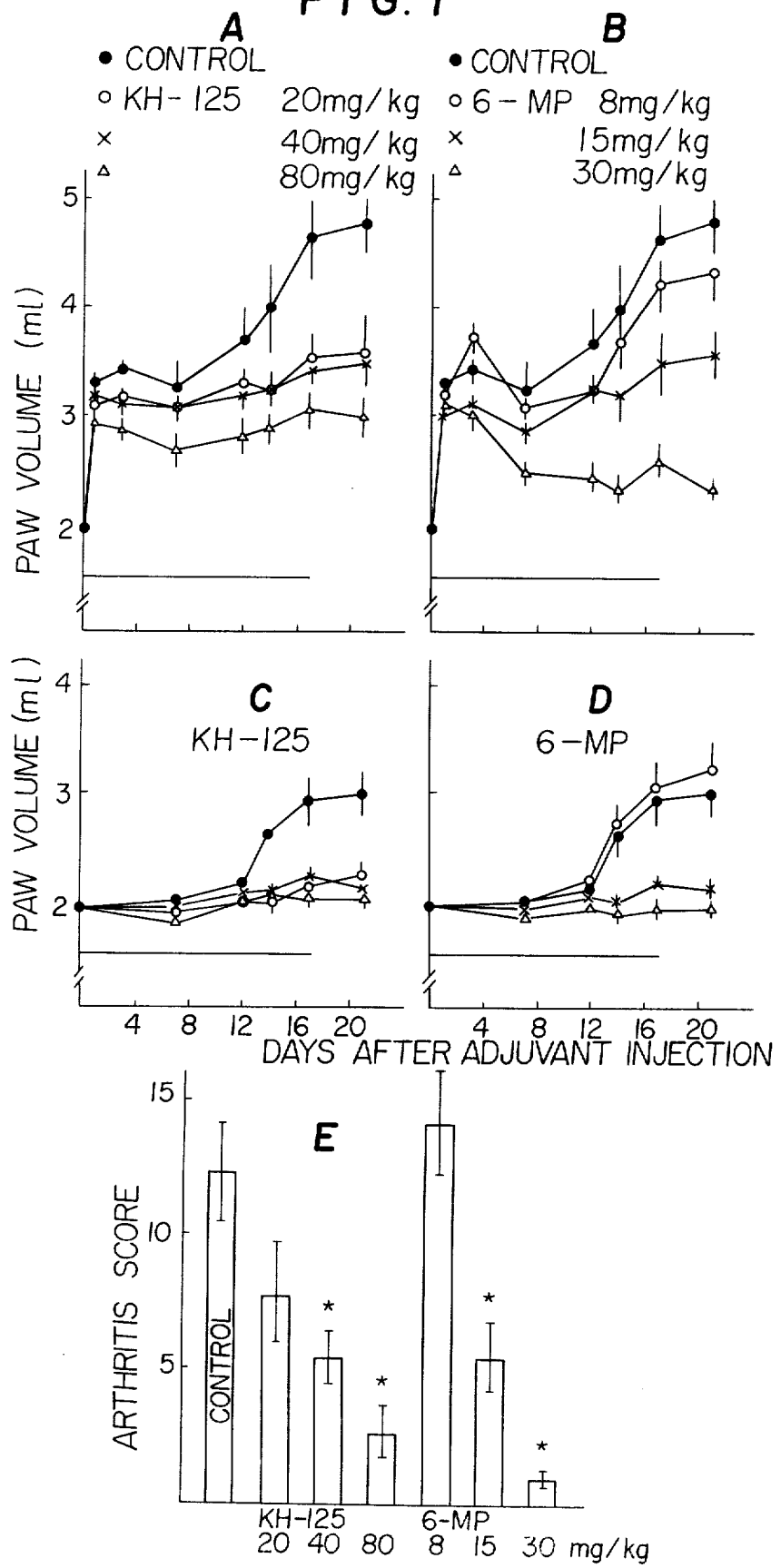

United States Patent [19]

Irikura

[11] 3,934,036

[45] Jan. 20, 1976

[54] N-BENZENESULFONYL-β-ALANINE HYDRAZIDE USEFUL AS AN IMMUNOSUPPRESSIVE AGENT

[75] Inventor: Tsutomu Irikura, Tokyo, Japan

[73] Assignee: Kyorin Seiyaku Kabushiki Kaisha, Japan

[22] Filed: Jan. 23, 1975

[21] Appl. No.: 543,772

[52] U.S. Cl. .......................... 424/321; 260/556 AR
[51] Int. Cl.² ........................................ A61K 31/18
[58] Field of Search ....... 424/321, 327; 260/556 AR

[56] References Cited
OTHER PUBLICATIONS
Irikura et al., Chem. Abst. Vol. 80 (1974), p. 82444M.

*Primary Examiner*—Sam Rosen
*Attorney, Agent, or Firm*—Wenderoth, Lind & Ponack

[57] ABSTRACT

The present invention relates to a valuable medicament for oral administration containing N-benzenesulfonyl-β-alanine hydrazide as an effective ingredient. The drug of this invention is useful, as an immunosuppressive agent, for suppression of so-called autoimmune diseases such as nephrotic syndromes, rheumatoid arthritis and systemic lupus erythematosus etc.

Furthermore, it may be possible to decrease or withdraw from dosing of corticosteroid by the use of KH-125 in a patient who has long been treated with that hormone.

5 Claims, 7 Drawing Figures

N-BENZENESULFONYL-β-ALANINE HYDRAZIDE USEFUL AS AN IMMUNOSUPPRESSIVE AGENT

The present invention relates to a valuable medicament for oral administration containing N-benzenesulfonyl-β-alanine hydrazide as an effective ingredient. The drug of this invention is useful, as an immunosuppressive agent, for suppression of so-called autoimmune diseases such as nephrotic syndromes, rheumatoid arthritis and systemic lupus erythematosus etc.

Furthermore, it may be possible to decrease or withdraw from dosing of corticosteroid by the use of KH-125 in a patient who has long been treated with that hormone.

This invention relates to pharmaceutical compositions: more particularly it relates to pharmaceutical compositions which are useful for the suppression of so-called autoimmune diseases.

Such immunosuppressive drugs as 6-mercaptopurine, azathioprine and cyclophosphamide have been used clinically for the treatment of rheumatoid arthritis, nephrotic syndromes, hepatitis and hemolytic anemia, all of which have been considered to belong to so-called autoimmune diseases. High toxicity of these drugs, however, has made it difficult to use clinically, especially to prescribe for a patient repeatedly for a long-term. Therefore an arrival of a novel immunosuppressive agent which has a wider safety margin without lowering its therapeutic effects has long been expected.

The investigations which lead to the discovery of the present invention are concerned with amino acid hydrazide derivatives having a potent immunosuppressive activity and low toxicity.

In an attempt to find an immunosuppressive agent having a lowered toxicity, about fifty acid hydrazides, mainly amino acid hydrazide derivatives, were synthesized and screened for their ability to suppress the antibody formation to sheep erythrocytes in mice. During these investigations, N-benzenesulfonyl-β-alanine hydrazide (KH-125) was found to have the most potent immunosuppressive activity and fairly lower acute toxicity among the compounds tested. Further detailed pharmacological and toxicological studies were then performed about KH-125.

In detailed pharmacological studies, KH-125 was confirmed to have the abilities in rats to suppress adjuvant arthritis as well as experimental nephrotoxic nephritis. Its toxicological properties were evaluated by subacute and chronic toxicity tests in rats, by teratological studies in rats and rabbits and also by carcinogenic tests in mice and rats. It was found from these studies that KH-125 had a considerably lower toxicity than well-known immunosuppressive agents did. Moreover KH-125 showed neither teratogenic nor carcinogenic effect, both of which were inevitably shared with established immunosuppressive drugs such as cyclophosphamide and 6-mercaptopurine etc.

Before the compound of this invention can be used medically, it must, of course, be formed into a pharmaceutical composition by association with a suitable pharmaceutical vehicle.

The term "pharmaceutical" is used herein to exclude any possibility that the nature of the vehicle, considered of course, in relation to the route by which the composition is intended to be administered, could be harmful rather than beneficial.

The choice of a suitable mode of presentation, together with an appropriate vehicle, is believed to be within the competence of those accustomed to the preparation of pharmaceutical formulations.

Accordingly this invention provides a pharmaceutical composition which comprises N-benzenesulfonyl-β-alanine hydrazide in association with a suitable pharmaceutical vehicle.

The compositions of this invention may be administered orally and in respect of these modes, the "pharmaceutical vehicle" is preferably: the ingestible excipient of a tablet, coated tablet, sublingnal tablet or pill; the ingestible container of a capsule or cachet; the ingestible pulverulent solid carrier of a powder; or the ingestible liquid medium of a syrup, solution, suspension or elixir.

In accompanying drawings:

FIG. 1 shows prophylactic effects of KH-125 and 6-MP on adjuvant arthritis. Drugs were orally administered once daily for 17 days starting from the day of adjuvant injection.

A, B: Changes in swelling of adjuvant injected foot.
C, D: Changes in swelling of adjuvant noninjected foot.
E: Arthritis score on day 21 after adjuvant injection.
*: Significantly different from control, $p < 0.01$.

Figure 2:
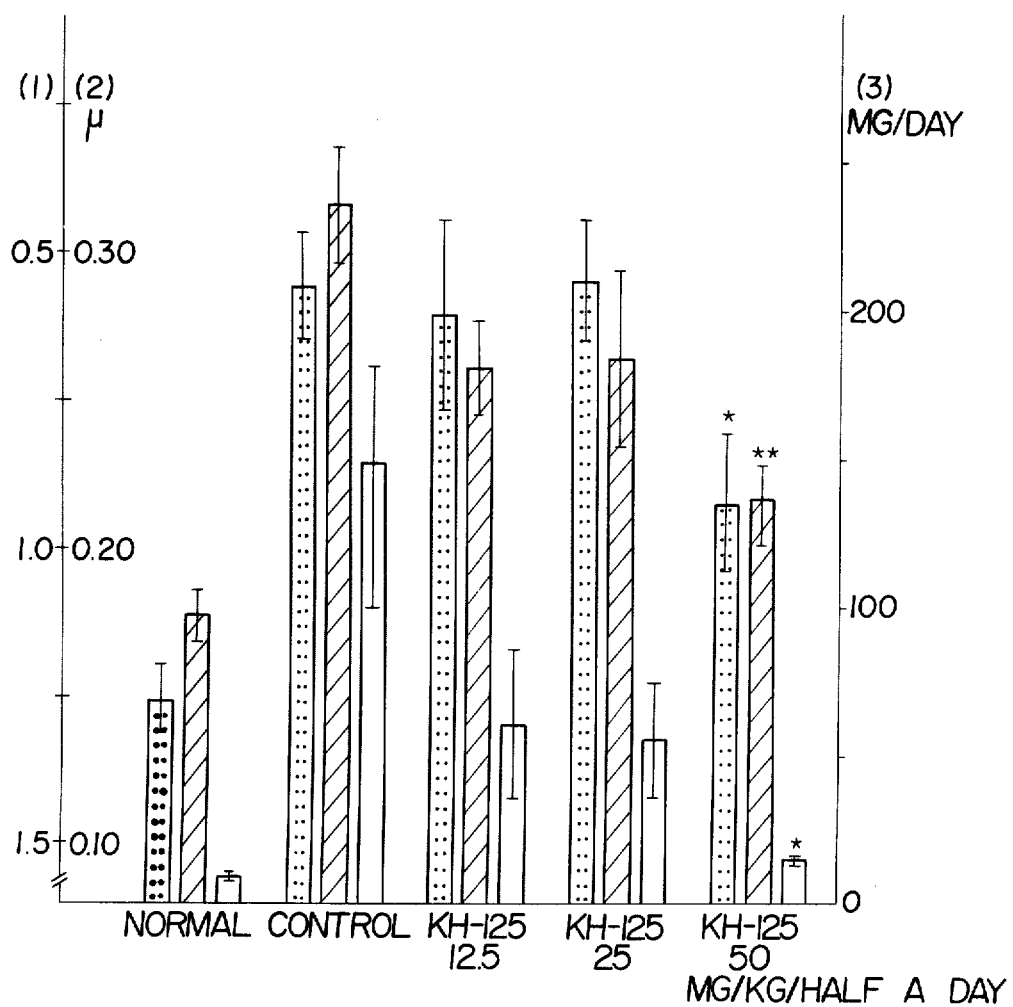

FIG. 2 shows effect of KH-125 on fusions index, thickness of basement membrane and protein-uria in nephrotic rats. Protein-uria was measured 18 days after nephrotoxin injection, then for electron microscopic examination the rats were killed 2 days later. Vertical lines show the standard error. *, ** Significantly different from control, $p < 0.05$ and $0.01$, respectively.

$$\text{Fusions index} = \frac{\text{number of foot process gaps}}{\text{length of glomerular capillary loop in outer pale layer}}$$

(1) Fusions index
(2) Thickness of basement membrane
(3) Protein-uria

Figure 3:
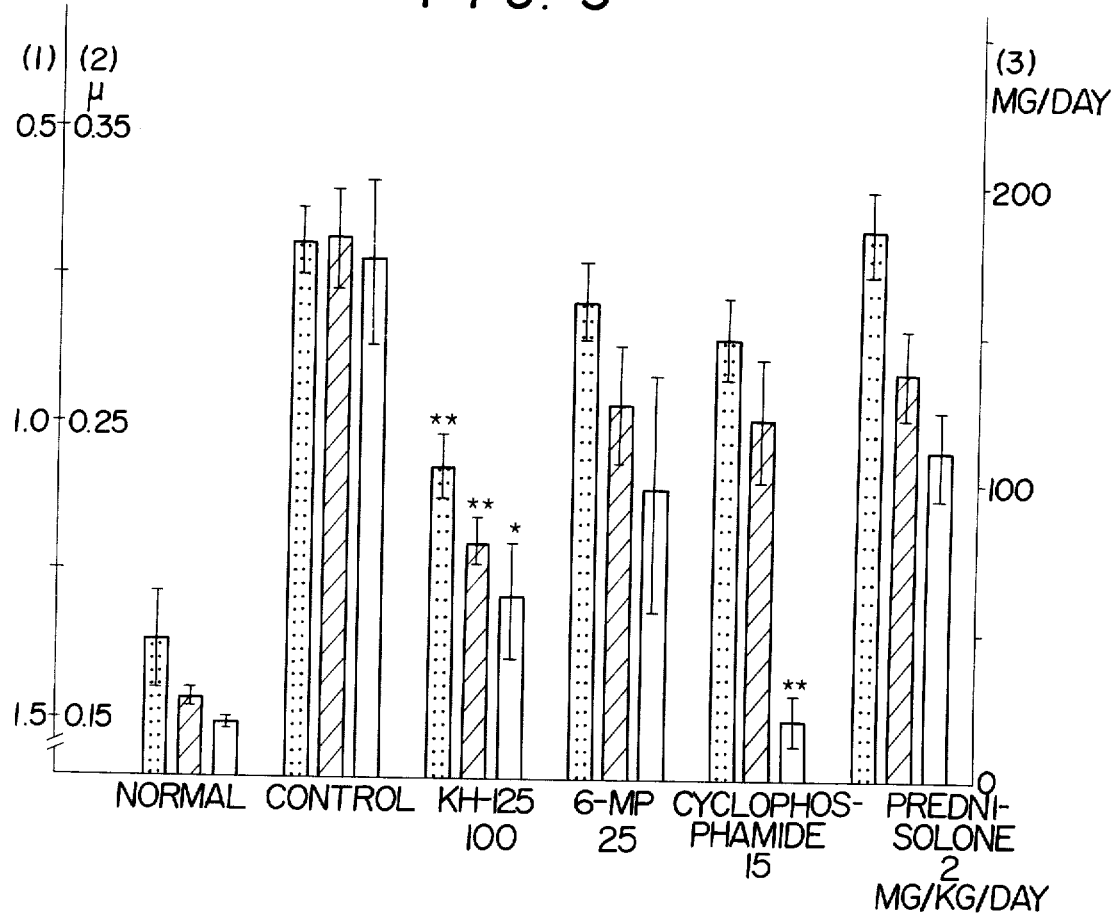

FIG. 3 shows comparison of KH-125 with other immunosuppressive agents in fusions index, thickness of basement membrane and protein-uria. Protein-uria was measured 18 days after nephrotoxin injection, then for electron microscopic examination the nephrotic rats were killed 3 days later. See legend of FIG. 2 for other details.

In order further to illustrate this invention but without being limited thereto, the following examples are given:

EXAMPLE 1

Preparation of N-Benzenesulfonyl-β-alanine hydrazide

To a solution of 7.5g of N-benzenesulfonyl-β-alanine ethyl ester in 20ml of ethanol, 2.1g of 80% hydrazine hydrate was added slowly and then the mixture was refluxed for 6 hrs. After cooling, crystals separated out were collected and recrystallized from ethanol to give 5.8g of N-benzenesulfonyl-β-alanine hydrazide in the form of colorless plates having a melting point of 135°–137°C.

Analysis: $C_9H_{13}N_3O_3S$ Calculated: C% 44.44; H% 5.39; N% 17.28; Found: 44.52; 5.41; 17.45.

EXAMPLE 2

Tablets are prepared by mixing and granulating, in accordance with known pharmaceutical techniques, the following ingredients.

| Ingredient | mg/tablet |
|---|---|
| KH-125 | 50 |
| Lactose | 105 |
| Corn starch | 25 |
| Magnesium stearate | 0.9 |
| 5% Hydroxypropyl cellulose | proper quantity |

EXAMPLE 3

Tablets are prepared by mixing, granulating, tableting and coating, in accordance with known pharmaceutical techniques, the following ingredients.

| Ingredient | mg/tablet |
|---|---|
| KH-125 | 50 |
| Lactose | 100 |
| Crystalline cellulose | 15 |
| Corn starch | 15 |
| Magnesium stearate | 0.9 |
| 5% Hydroxypropyl cellulose | proper quantity |

EXAMPLE 4

Capsules are prepared in accordance with known pharmaceutical techniques, for example using the following ingredients.

| Ingredient | mg/capsule |
|---|---|
| KH-125 | 50 |
| Lactose | 100 |
| Corn starch | 100 |
| Magnesium stearate | 1 |

EXAMPLE 5

One pulverulenta is prepared, in accordance with known pharmaceutical techniques, from the following ingredients.

| Ingredient | mg/pulverulenta |
|---|---|
| KH-125 | 50 |
| Lactose | 450 |

EXAMPLE 6

A suspension for oral administration is prepared, in accordance with known pharmaceutical techniques, from the following ingredients.

| Ingredient | |
|---|---|
| KH-125 | 50 mg |
| Sodium carboxymethyl cellulose | 300 mg |
| Simple syrup | 50 ml |

EXAMPLE 7

Granules are prepared, in accordance with known pharmaceutical techniques, from the following ingredients.

| Ingredient | |
|---|---|
| KH-125 | 50 mg |
| Lactose | 30 mg |
| Potato starch | 15 mg |
| Crystalline cellulose | 20 mg |
| 5% Hydroxypropyl cellulose | proper quantity |

EXPERIMENT A

Acute Toxicity of N-Benzenesulfonyl-$\beta$-alanine hydrazide (KH-125)

The acute toxicity of KH-125 was studied in both sexes of ddY mice and Wistar rats. The $LD_{50}$ values were calculated by the method of Litchfield and Wilcoxon (J. Pharmacol. Exptl. Ther., 96, 99, 1949).

The $LD_{50}$ (mg/kg) values of KH-125 were as follows: 1520 (p.o.), 1230 (i.p.) and 1150 (s.c.) in male mice; 1570 (p.o.), 1410 (i.p.) and 1440 (s.c.) in female mice; >4000 (p.o.), 2150 (i.p.) and >4000 (s.c.) in male rats; >4000 (p.o.), 2580 (i.p.) and >4000 (s.c.) in female rats. No sex difference concerning the acute toxicity was apparent.

EXPERIMENT B

Chronic Toxicity Study on N-Benzenesulfonyl-$\beta$-alanine hydrazide (KH-125)

The chronic toxicity study of KH-125 was carried out in Wistar rats of both sexes. Rats were treated orally with KH-125 for 6 months at the dose levels of 0 (control), 10, 20 and 40 mg/kg/day.

All rats survived after 6-month treatment with KH-125. The body weight gain was slightly inhibited in the 40 mg/kg/day groups. Hematological findings revealed the dose-dependent decrease in erythrocyte count and hemoglobin. No remarkable changes were observed in serum enzyme activities by the treatment with KH-125 except that slight but dose-dependent increases in S-GOT and S-GPT were found. No significant effects on general symptoms, food intake, urinalysis, and fractionation of serum protein were observed. No toxic effects which could be attributed to the drug were detected in the histopathological examinations.

EXPERIMENT C

Suppressive Effect of N-Benzenesulfonyl-$\beta$-alanine hydrazide (KH-125) on Antibody Production to Sheep Erythrocytes The effect of KH-125 on antibody production in ddY mice was examined by Cunningham and Szenberg's plaque technique (Immunology, 14, 599, 1968) and compared with other agents.

Mice were immunized by intravenous injection of washed sheep erythrocytes (4 × $10^8$ cells/mouse). Administration of KH-125 was made orally for 4 consecutive days from the day of antigen injection. 19S Plaque-forming cells (PFC) were counted 4 days after immunization. As shown in Table 1, KH-125 dose-dependently suppressed the appearance of 19S PFC.

In comparative experiment, test agents were administered intraperitoneally for 8 consecutive days from one day before immunization. 7S PFC's were counted 9 days after immunization. As shown in Table 2, suppressive effect of KH-125 on the appearance of 7S PFC was higher than that of prednisolone or 6-mercaptopurine, but was less effective than cyclophosphamide.

Table 1

Effect of KH-125 on the number of 19S plaque-forming cells (Oral administration)

| Dose (mg/kg/day) | No. of mice | Mean body weight gain (g) | Spleen weight mean ± S.E. (mg) | 19S PFC/10⁶ spleen cells mean ± S.E. |
|---|---|---|---|---|
| Control | 4 | +0.8 | 181 ± 8 | 1905 ± 267 |
| 40 | 4 | +1.0 | 135 ± 20 | 1383 ± 327 |
| 80 | 4 | −0.8 | 139 ± 9* | 368 ± 124** |
| 160 | 4 | −0.5 | 164 ± 14 | 329 ± 46 ** |

*, ** : Significantly different from control, p < 0.05 and 0.01, respectively.

Table 2

Comparison of immunosuppressive effect of KH-125 with other agents

| Agents | Dose (mg/kg/day) | No. of mice | Mean body weight gain (g) | Spleen weight mean ± S.E. (mg) | 7SPFC*/10⁶ spleen cells mean ± S.E. |
|---|---|---|---|---|---|
| control | | 6 | +1.0 | 125 ± 16 | 1045 ± 202 |
| KH-125 | 200 | 6 | −4.5 | 60 ± 8 *** | 233 ± 63 *** |
| 6-mercapto- purine | 30 | 6 | 0 | 103 ± 12 | 385 ± 83 ** |
| cyclophos- phamide | 20 | 6 | +0.2 | 87 ± 7** | 61 ± 8 *** |
| prednisolone | 4 | 6 | +1.6 | 116 ± 19 | 706 ± 178 |

Agents were administered intraperitoneally for 8 consecutive days from one day before immunization. Plaque-forming cells were counted 9 days after immunization.
* Addition of rabbit anti-mouse γG sera.
, * Significantly different from control, p < 0.05 and 0.01, respectively.

EXPERIMENT D

Suppressive Effect of N-Benzenesulfonyl-β-alanine hydrazide (KH-125) on Adjuvant Arthritis in Rats The effect of KH-125 on adjuvant arthritis in rats was compared with that of 6-mercaptopurine. Sprague-Dawley rats were given with a single intradermal injection of 0.01 ml of a liquid paraffin oil suspension of *Mycobacterium tuberculosis* (concentration, 5 mg/ml) into the subplantar area of a right hind paw. Test agents were administered orally once a day for 17 days starting from the day of adjuvant-injection. Volumes of right and left hind feet were determined volumetrically by immersing the feet into water. Arthritis score was obtained by visual observation and graded from 0 to 4+.

In the prophylactic experiment on adjuvant arthritis, both KH-125 and 6-mercaptopurine dose-dependently suppressed the swelling of adjuvant-injected and non-injected feet as well as the increase in arthritis score (FIG. 1). Three of 7 rats treated with 30 mg/kg/day of 6-mercaptopurine died during the experiment, but those which were given with KH-125 at a dose of as high as 80 mg/kg/day survived throughout the test period. When comparison was made between two drugs with respect to safety margin— i.e., maximal tolerated dose in repeated administration versus effective dose in suppression of adjuvant arthritis— KH-125 was considered to be about 3 times as safe as 6-mercaptopurine.

Rebound of foot swelling occurring after withdrawal of KH-125 was not prominent.

EXPERIMENT E

Suppressive Effect of N-Benzenesulfonyl-β-alanine hydrazine (KH-125) on Nephrotoxic Nephritis in Rats The effect of KH-125 on nephrotoxic nephritis in Wistar rats was evaluated from the following three points: (1) urinary protein measurements, (2) electron microscopic findings and (3) light microscopic findings. Nephrotic rats were prepared according to Shibata's method. (Ths Saishin-Igaku, 20, 1089, 1965).

In a prophylactic experiment, KH-125 was orally administered twice a day for 18 days during 21 days from 2 days before nephrotoxin-injection to 18 days after the injection. Urinary protein was measured 18 days after the nephrotoxin-injection, and then the nephrotic rats were sacrificed 2 days later for histopathological examinations. As shown in FIG. 2, protein-uria was decreased dose-dependently by the treatment with KH-125. In electron microscopic findings, it was observed that fusion index of epithelial foot processes was improved and thickening of glomerular basement membrane was suppressed by the treatment with KH-125. Light microscopic findings also showed a good improvement of nephritis in the animals treated with KH-125.

In a comparative experiment, test agents were administered once daily: KH-125, 15 days during days 0 – 10 and 15 – 18 (p.o.); 6-mercaptopurine (6-MP), 6 days during days 0 – 5 (p.o.); cyclophosphamide, 11 days during days 0 – 10 (i.p.); and prednisolone, 11 days during days 0 – 10 (i.p.), starting from the day of nephrotoxin-injection. Urinary protein was measured 18 days after the injection of nephrotoxin, and then the animals were sacrificed 3 days later for histopathological examinations. As shown in FIG. 3, the nephrotoxic nephritis was most effectively suppressed in the group treated with KH-125 as judged from the decrease in protein-uria, improvement of fusion index of epithelial foot processes and suppression of thickening of glomerular basement membrane.

What is claimed is:

1. A pharmaceutical composition in oral dosage unit form comprising a pharmaceutical carrier and from about 20 to 400 mg per unit of N-benzenesulfonyl-β-alanine hydrazide.

2. A pharmaceutical composition in accordance with claim 1, in which a solid pharmaceutical carrier is employed.

3. A pharmaceutical composition in accordance with claim 1, in which a liquid pharmaceutical carrier is employed.

4. A method of treating autoimmune disease in the human body comprising administering an effective amount of the composition of claim 1.

5. A method of treating autoimmune disease in the human body comprising administering a therapeutic composition in oral dosage unit form comprising a pharmaceutical carrier and an effective amount of N-benzenesulfonyl-β-alanine hydrazide.

* * * * *